Dec. 30, 1958 H. C. SWIM Plant Pat. 1,787
PEACH TREE
Filed Jan. 7, 1958
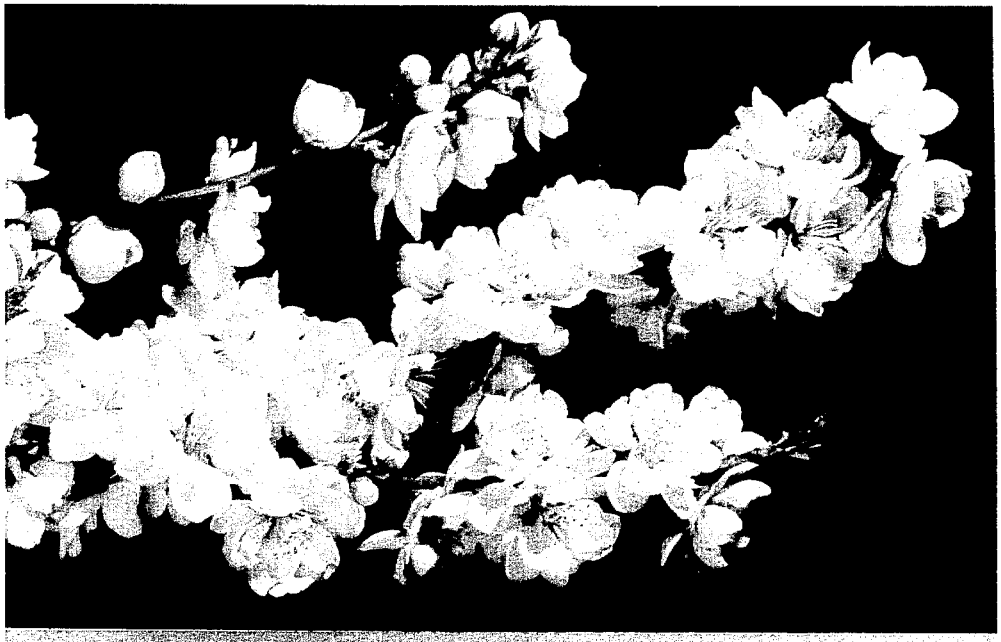
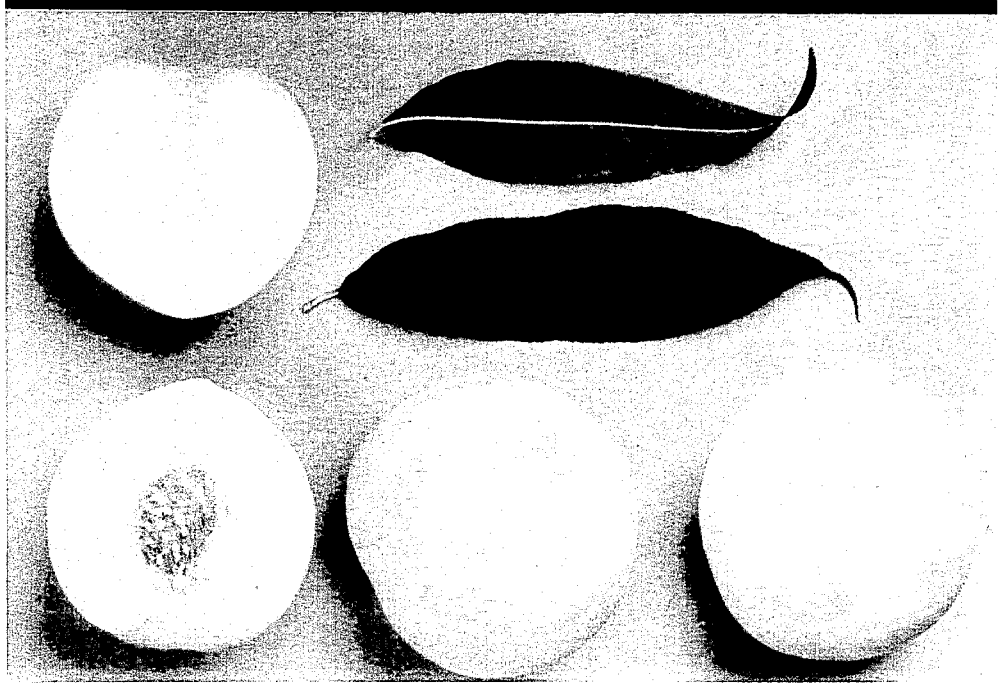
Inventor.
H. C. Swim
By: Robb & Robb
Attorneys.

United States Patent Office

Plant Pat. 1,787
Patented Dec. 30, 1958

1,787

PEACH TREE

Herbert C. Swim, Ontario, Calif., assignor to Armstrong Nurseries, Inc., Ontario, Calif., a corporation of California Application January 7, 1958, Serial No. 707,657

1 Claim. (Cl. 47—62)

The present invention relates to a new and distinct variety of peach tree of the yellow-fleshed, freestone, fruit-bearing and ornamental flowering type, which was originated by me as a seedling derived from crossing two unnamed and unpatented varieties, each of the latter being derived from an extended series of crosses involving the varieties "Early Imperial" (unpatented), "Coolidge Double Red" (unpatented), "Rio Oso Gem" (Plant Patent No. 84), "Socala" (unpatented) and "Chinese Dwarf" (unpatented), in the case of the seed parent, and "Rio Oso Gem" (Plant Patent No. 84), "Luken's Honey" (unpatented), and "Peppermint" (unpatented), in the case of the pollen parent.

The primary objective of this breeding was to produce an improved fruiting-flowering peach variety by combining the large, showy, double-flower characteristics of the flowering type peaches "Coolidge Double Red" and "Peppermint" with the high fruit quality of the fruiting type peaches "Rio Oso Gem," "Early Imperial" and "Socala." This objective was fully achieved, as evidenced by the following dominent features of my new variety, which represent a unique combination and distinguish the new variety from its parents, as well as from all other varieties of which I am aware:

(1) A medium vigorous habit of tree growth, with a chilling requirement slightly less than that of "July Elberta" (Plant Patent No. 15);

(2) Large, double flowers of light pink color, which are borne from 1 to 3 flowers per node, with the nodes relatively closely spaced, and giving a distinctive ornamental appearance to the tree during the blooming period;

(3) Large, yellow-fleshed, freestone fruit having a good, sweet, relatively mild peach flavor; and (4) A fruit-ripening habit averaging about one week ahead of that of "July Elberta" in early midseason in southern California.

The new variety more nearly resembles the variety "Saturn" (Plant Patent No. 1,485) than any other variety, but is distinguished therefrom by its light pink flowers, in contrast to the medium pink flowers of "Saturn"; its fruit maturation period is from about a week to ten days shorter, on the average, than that of "Saturn"; it has a higher chilling requirement than "Saturn"; it has only a medium vigorous habit of growth in contrast to the very vigorous habit of growth of "Saturn"; and the fruit of the new variety is mild and sweet in flavor, in contrast to the stronger, more acid flavor of the fruit of "Saturn."

Asexual reproduction of the new variety by grafting, as performed at Ontario, California, shows that the foregoing characteristics and distinctions come true to form and are established and transmitted through succeeding propagations.

The accompanying drawing shows typical specimens of the flowers, foliage and fruit of my new variety, with the upper and lower surfaces of the foliage being illustrated, and with both exterior and sectional views of the fruit being shown, all as depicted in color as nearly true as it is reasonably possible to make the same in a color illustration of this character.

The following is a detailed description of my new variety, as based upon observations of specimens grown at Ontario, California, with color terminology in accordance with Robert F. Wilson's Horticultural Colour Chart, except where general color terms of ordinary dictionary significance are obvious:

Tree: Upright-spreading; productive; medium vigorous.

*Current growth.* — Smooth; with cracked, slightly raised lenticels toward the base of the more vigorous shoots. Color—green, but slightly reddish on exposed surfaces, with numerous small, near white dots; ultimately becoming brown.

*2-year wood.*—Has slightly raised, irregular, longitudinal striations and numerous lenticels. Color—from greenish brown to brown.

*Old wood.*—Relatively smooth, with moderate number of large, raised lenticels and occasional deep longitudinal fissures. Color—from gray to grayish brown, with reddish brown on more exposed surfaces.

*Leaves.*—Abundant. Size—from 5 to 6 inches long; from 1 inch to 1½ inches wide. Shape—lanceolate, with apex acuminate. Color: upper surface—dark green; lower surface—lighter green. Petiole—medium length. Margin—finely serrate; glandular. Glands—reniform; medium size; usually 2 or 3 in number; borne on petiole and more rarely on the base of the blade; arranged alternately.

*Vegetative buds.*—Small; ovoid (unless compressed between flower buds); pubescent. Color—dark brown.

Flowers:

*Dormant buds.* — Ovoid; with pubescent scales. Color—dark brown.

*"Pink bud" stage.*—Globular. Color—near Neyron Rose, Plate 623/2, page 76, with petal margins near Neyron Rose, Plate 623/1, page 76.

*Dates of first and full bloom.*—Over prolonged period varied rather widely from about February 27th to about March 19th, and from about March 16th to March 29th, respectively, due to weather variations from year-to-year.

*Size (when fully open).*—Showy; large; from about 1¾ inches to about 2 inches in diameter when tree has been winter-pruned well ahead of bloom.

*Petalage.*—Double; usually from 14 to 18 petals, with an occasional petaloid.

*Petals.*—Arranged regularly; cupped and sometimes wavy, with petaloids twisted and irregular. Shape—nearly oval; rounded at apex and base; tapering toward point of attachment. Margins—entire, except for occasional notching at apical end.

*Flower color.*—Near Neyron Rose, Plate 623/3, page 76, with traces of near Neyron Rose, Plate 623/2, page 76.

*Spacing of flowers.*—From 1 to 3 flowers borne at nearly every node, with nodes usually spaced from ½ inch to 1 inch apart on flowering branches, thereby forming an almost continuous spray of flowers along each branch and giving the tree a definite ornamental appearance during the blooming period.

Fruit:

*Ripening date.*—Usually ripens about one week ahead of "July Elberta" in early to mid-July at Ontario, California, with commencement of first ripening varying rather widely over a prolonged period of observation, from about July 5th to about July 22nd.

*Maturity when described.*—Eating ripe.

*Size.*—Somewhat variable, but ranging from medium to large when well thinned. Axial diameter—from about 2⅝ inches to about 3 inches. Transverse diameter in suture plane—from about 2⅜ inches to about 2⅝ inches. Diameter at right angles to suture plane—from about 2⅝ inches to 3 inches.

*Form.*—Somewhat variable; broadly ovoid; compressed laterally toward suture plane.

*Suture.*—Usually shallow; extends from base to apex; has slight depression beyond pistil point.

*Ventral surface.*—Rounded; sometimes slightly lipped throughout on right side.

*Cavity.*—Rounded; elongated slightly in suture plane; with suture showing on one side. Depth—from about ⅜ inch to about ½ inch. Width—from about ⅝ inch to about ¾ inch.

*Base.*—Rounded.

*Apex.*—Usually short, but sometimes prolonged, with pistil point short and oblique.

*Stem.*—From about ¼ inch to about ⅜ inch in length; medium caliper; glabrous; strong adherence to stone.

*Skin.*—Average thickness and tenderness; tenacious to flesh; moderate pubescence of medium length. Color—between Indian Yellow, Plate 6/2, page 6 and Chinese Yellow, Plate 606/2, page 68, and somewhat streaked, flecked and blushed with from near Claret Rose, Plate 021/1, page 109 to near Claret Rose, Plate 021/2, page 109.

*Flesh.*—Texture—firm; melting; with abundant, relatively fine, tender fibres. Aroma — moderate. Flavor — excellent; subacid; sweet; mild peach flavor. Color—near Lemon Yellow, Plate 4/2, page 4, with surface of pit cavity between Lemon Yellow, Plate 4/2, page 4 and Buttercup Yellow, Plate 5/2, page 5; sometimes with a faint trace between fibres of from near Geranium Lake, Plate 20/2, page 20, to near Geranium Lake, Plate 20/3, page 20.

Stone: Free, except for some adherence to flesh along both dorsal and ventral edges toward base, and sometimes short, fibre-like threads are retained along ridges.

*Size.*—Length—from about 1¼ inches to about 1½ inches. Width—from about ⅞ inch to about 1 inch. Thickness—from about ⅝ inch to about ¾ inch.

*Form.*—Obovoid.

*Base.*—Somewhat oblique.

*Hilum.*—Oval.

*Apex.*—Acute.

*Sides.*—Equal, with surface irregularly furrowed and pitted throughout.

*Ridges.*—Rounded.

*Pits.*—Circular and sometimes elongated.

*Ventral edge.*—Medium thick; with wing toward base.

*Dorsal edge.*—Narrow, with shallow, narrow groove; ridges on either side interrupted.

*Color.*—Brown.

I claim:

A new and distinct variety of peach tree of the yellow-fleshed, freestone, fruit-bearing and ornamental flowering type, substantially as herein shown and described, characterized particularly as to novelty by the combination of a medium vigorous habit of growth, a slightly less chilling requirement than that of the variety "July Elberta" (Plant Patent No. 15), large, double flowers of light pink general color tonality which are borne from 1 to 3 flowers per node, with the nodes relatively closely spaced and giving a distinctly ornamental appearance to the tree during its blooming period, large freestone fruit which has a good, sweet, relatively mild peach flavor, and a fruit-ripening habit averaging about 1 week earlier than that of the variety "July Elberta" in early mid-season in southern California.

No references cited.